(12) United States Patent
Hara et al.

(10) Patent No.: US 9,856,507 B2
(45) Date of Patent: Jan. 2, 2018

(54) METHOD FOR SCREENING FOOD INGREDIENTS AND FOOD COMPOSITIONS

(71) Applicant: JAPANESE FOUNDATION FOR CANCER RESEARCH, Tokyo (JP)

(72) Inventors: Eiji Hara, Tokyo (JP); Naoko Ohtani, Tokyo (JP); Shin Yoshimoto, Tokyo (JP); Tze Mun Loo, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 127 days.

(21) Appl. No.: 14/767,166

(22) PCT Filed: Feb. 10, 2014

(86) PCT No.: PCT/JP2014/053047
§ 371 (c)(1),
(2) Date: Aug. 11, 2015

(87) PCT Pub. No.: WO2014/126043
PCT Pub. Date: Aug. 21, 2014

(65) Prior Publication Data
US 2016/0002699 A1    Jan. 7, 2016

(30) Foreign Application Priority Data

Feb. 12, 2013   (JP) ................. 2013-025030

(51) Int. Cl.
| | |
|---|---|
| C12Q 1/00 | (2006.01) |
| C12Q 1/18 | (2006.01) |
| C12Q 1/02 | (2006.01) |
| G01N 33/02 | (2006.01) |
| G01N 33/50 | (2006.01) |

(52) U.S. Cl.
CPC .............. *C12Q 1/18* (2013.01); *C12Q 1/025* (2013.01); *G01N 33/02* (2013.01); *G01N 33/5011* (2013.01); *G01N 2333/33* (2013.01)

(58) Field of Classification Search
CPC ..................................................... C12Q 1/18
See application file for complete search history.

(56) References Cited

FOREIGN PATENT DOCUMENTS

| | | |
|---|---|---|
| JP | 2001-253829 | 9/2001 |
| JP | 2004-244365 | 9/2004 |
| JP | 2006-56839 | 3/2006 |
| JP | 2011-184311 | 9/2011 |
| JP | 2012-025691 | 2/2012 |

OTHER PUBLICATIONS

Wu et al (J. Agric. Food Chem. vol. 59, pp. 989-994, 2011).*
International Search Report dated Apr. 8, 2014, Application No. PCT/JP2014/053047, English translation included.
Yoshimoto et al., "Obesity-induced gut microbial metabolite promotes liver cancer through senescence secretome", Nature, Jul. 4, 2013, pp. 97-101, vol. 499.
Sharpless, NE and DePinho, RA, "Cancer: Crime and punishment", Nature, Aug. 4, 2005, pp. 636-637, vol. 436.
Adams, "Healing and Hurting: Molecular Mechanisms, Functions, and Pathologies of Cellular Senescence", Molecular Cell, Oct. 9, 2009, pp. 2-14, vol. 36.
Collado, M. and Serrano M., "Senescence in tumors: evidence from mice and humans", Nature Reviews Cancer, Jan. 2010, pp. 51-57, vol. 10.
Kuilman, et al., "The essence of senescence", Genes & Development, 2010, pp. 2463-2479, vol. 24.
Coppe, et al., "Senescence-Associated Secretory Phenotypes Reveal Cell-Nonautonomous Functions of Oncogenic RAS and the p53 Tumor Suppressor", PLoS Biology, Dec. 2008, pp. 2853-2868, vol. 6, Issue 12.
Rodier, F. and Campisi, J., "Four faces of cellular senescence", J. Cell Biol., 2011, pp. 547-556, vol. 192, No. 4.
Kuilman, T. and Peeper, D., "Senescence-messaging secretome: SMS-ing cellular stress", Nature Reviews Cancer, Feb. 2009, pp. 81-94, vol. 9.
Ohtani, N. and Hara, E., "Roles and mechanisms of cellular senescence in regulation of tissue homeostasis", Cancer Science, May 2013, pp. 525-530, vol. 104, No. 5.
Davalos, et al., "Senescent cells as a source of inflammatory factors for tumor progression", Cancer Metastasis Rev, 2010, pp. 273-283, vol. 29.
Ohanna, et al., "Senescent cells develop a PARP-1 and nuclear factor-kB-associated secretome (PNAS)", Genes & Development, 2011, 25:1245-1261.
Nagashima, et al., "Phylogenetic Analysis of 16S Ribosomal RNA Gene Sequences from Human Fecal Microbiota and Improved Utility of Terminal Restriction Fragment Length Polymorphism Profiling", Bioscience Microflora, 2006, pp. 99-107, vol. 25.
Japanese Office Action dated Oct. 20, 2015, 5 pages.
Xie, et al., "Effects of Two Lactobacillus Strains on Lipid Metabolism and Intestinal Microflora in Rats Fed a High-Cholesterol Diet"; BMC Complementary and Alternative Medicine, Jun. 3, 2011, vol. 11, No. 53, 14 pages.
Hu, et al., "Effects of NS Lactobacillus Strains on Lipid Metabolism of Rats Fed a High-Cholesterol Diet", Lipids in Health and Disease, May 9, 2013, vol. 12, No. 67, 14 pages.

* cited by examiner

*Primary Examiner* — Albert M Navarro
(74) *Attorney, Agent, or Firm* — Rankin, Hill & Clark LLP

(57) ABSTRACT

The present invention provides a method for screening for a food ingredient or a food composition that reduces a cancer risk and inhibits cancer development. A substance that reduces a cancer risk is screened by administering a candidate substance and analyzing alteration in gut microbiota or a metabolite produced by an intestinal bacterium. Also, candidate substances are screened by adding each candidate substance to a bacterial culture system and analyzing its effect on a bacterium involved in cancer development.

4 Claims, 8 Drawing Sheets

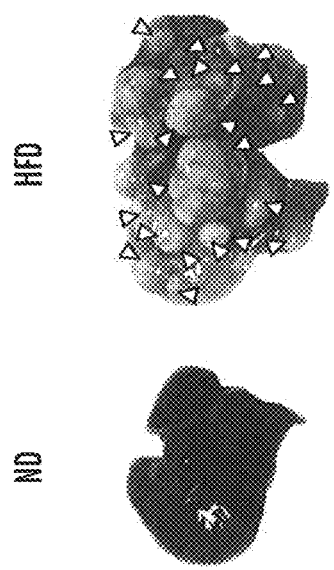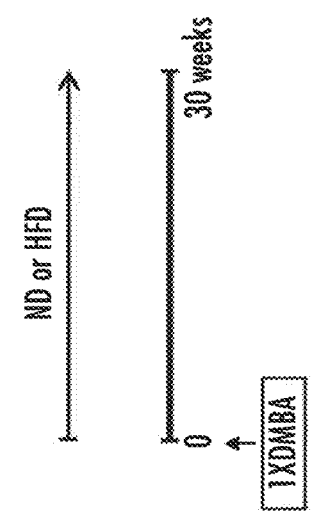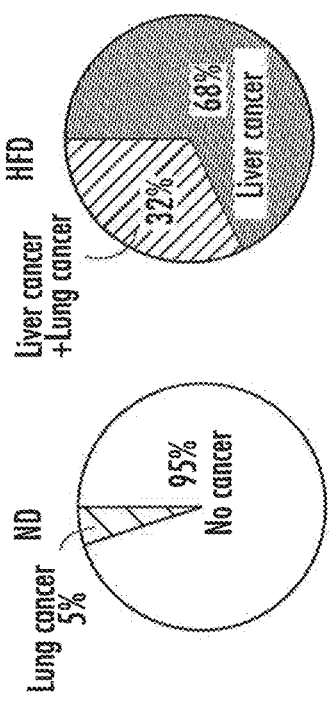

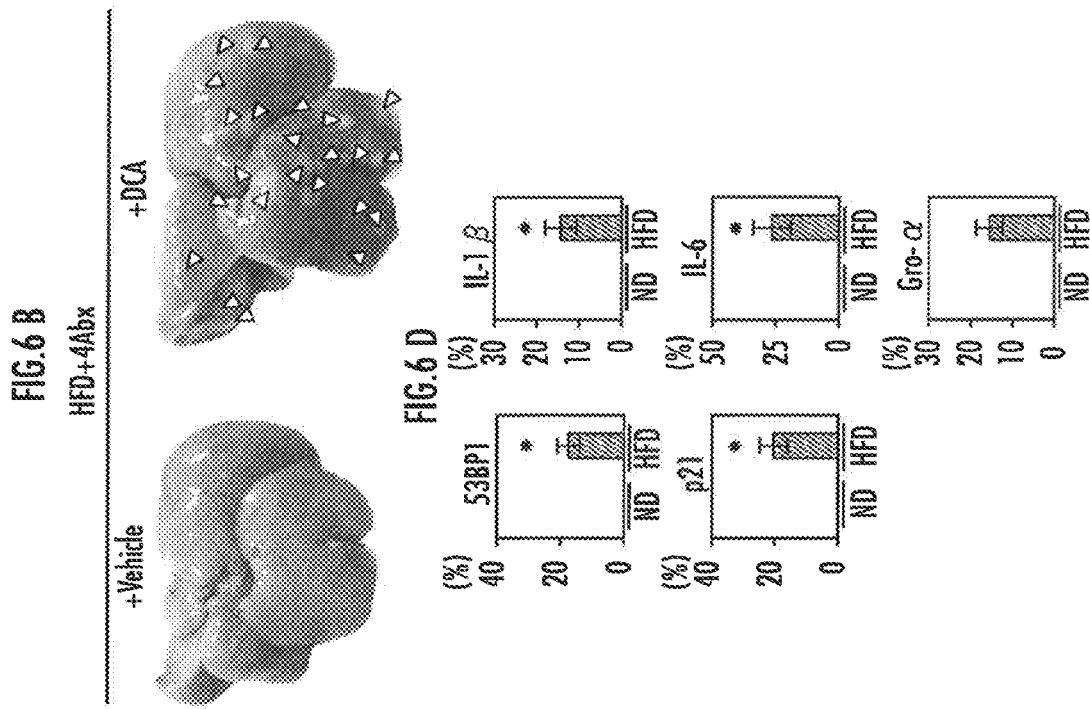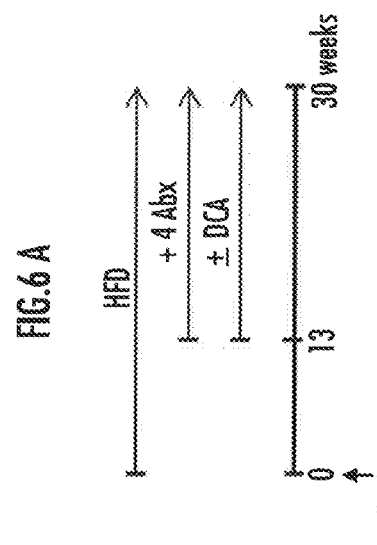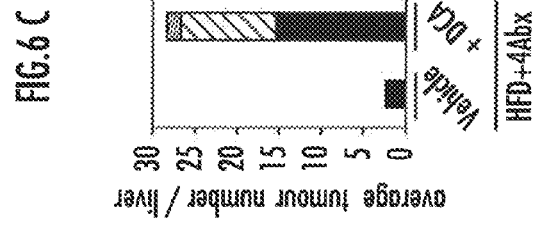

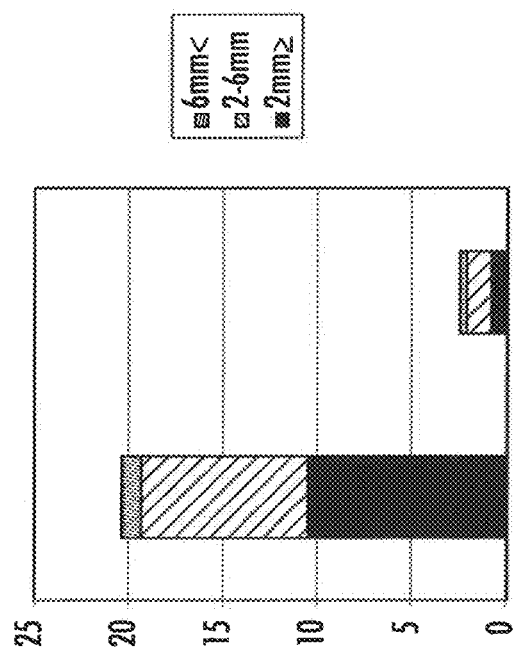
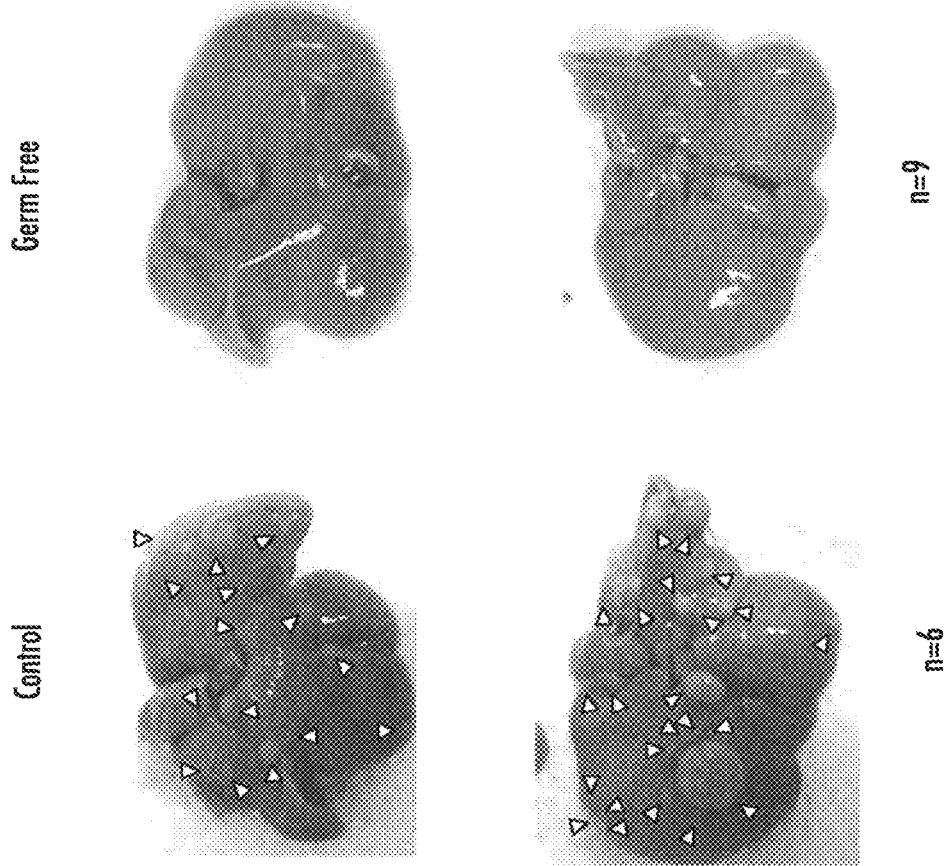

METHOD FOR SCREENING FOOD INGREDIENTS AND FOOD COMPOSITIONS

TECHNICAL FIELD

The present invention relates to a method for screening for a food ingredient that reduces a carcinogenic risk by improving gut microbiota balance.

BACKGROUND ART

Cancers are diseases caused by multiple stages of gene mutations and have been found to occur due to the damage of some genes so that cells continue to increase without limitations. In normal cells, even if genes are damaged by the stress causing DNA damage, this damage is usually repaired by a repair mechanism. However, when cells are placed under strong stress, cell death called apoptosis occurs or cell cycle halts at a cell cycle checkpoint to irreversibly terminate cell growth. This phenomenon in which cell growth is irreversibly terminated is called "senescence" and considered as an important cancer inhibition mechanism comparable to apoptosis (Non Patent Literatures 1 to 4).

Unlike apoptosis, the occurrence of senescence does not immediately induce cell death, and instead, the cells continue to survive for a long period in vivo. Recently, it has been revealed that once senescence occurs, various inflammatory cytokines are secreted in large amounts (Non Patent Literatures 5 and 6). This inflammatory cytokine secretion phenomenon associated with the senescence is called senescence-associated secretory phenotype (SASP) or senescence-messaging secretome (SMS), suggesting the possibility that this phenomenon is one of the causes of chronic inflammation or carcinogenesis based on chronic inflammation (Non Patent Literatures 5 to 7).

CITATION LIST

Non Patent Literature

Non Patent Literature 1: Sharpless N E, DePinho R A., Cancer: crime and punishment., Nature. (2005) Vol. 436 (7051): 636-7
Non Patent Literature 2: Adams P. D., Healing and hurting: molecular mechanisms, functions, and pathologies of cellular senescence., Mol Cell. (2009) Vol. 36 (1): 2-14.
Non Patent Literature 3: Collado M., & Serrano, M. Senescence in tumours: evidence from mice and humans., Nat Rev Cancer. (2010) Vol. 10 (1): 51-7.
Non Patent Literature 4: Kuilman, T. et al. The essence of senescence. Genes Dev. (2010) Vol. 24, 2463-2479.
Non Patent Literature 5: Coppe J. P., et al., Senescence-associated secretory phenotypes reveal cell-nonautonomous functions of oncogenic RAS and the p53 tumor suppressor., PLoS Biol. (2008) Vol. 6 (12): 2853-68.
Non Patent Literature 6: Rodier F., & Campisi, J., Four faces of cellular senescence., J Cell Biol. (2011) Vol. 192 (4): 547-56.
Non Patent Literature 7: Kuilman, T. & Peeper, D. S., Senescence-messaging secretome: SMS-ing cellular stress. Nature Rev. Cancer (2009) Vol. 9, 81-94.
Non Patent Literature 8: Ohtani N. and Hara E., Roles and mechanisms of cellular senescence in regulation of tissue homeostasis., (2013) Cancer Sci.
Non Patent Literature 9: Davalos et al., Senescent cells as a source of inflammatory factors for tumor progression., Cancer Metastasis (2010) June; 29 (2): 273-283.
Non Patent Literature 10: Ohanna et al., Senescent cells develop a PARP-1 and nuclear factor-kB-associated secretome (PNAS), Genes Dev. (2011) 25: 1245-1261.
Non Patent Literature 12: Nagashima K. et al., Phylogenetic Analysis of 16S Ribosomal RNA Gene Sequences from Human Fecal Microbiota and Improved Utility of Terminal Restriction Fragment Length Polymorphism Profiling. (2006) Bioscience and Microflora, Vol. 25, No. 3, pp. 99-107.

SUMMARY OF INVENTION

Technical Problem

However, the relation of SASP and the carcinogenic mechanism remains poorly understood. The present inventors have developed carcinogenesis models with multiple liver cancer and lung cancer and analyzed the carcinogenic mechanism. As a result, the present inventors have revealed that the proportion of Gram-positive bacteria is elevated due to alteration in gut microbiota so that the concentration in blood of deoxycholic acid produced by the Gram-positive bacteria is elevated. The present inventors have further found the mechanism in which the deoxycholic acid causes the senescence of hepatic stellate cells, which in turn secrete SASP factors, thereby promoting the carcinogenesis of hepatocytes in the neighborhood thereof.

The mechanism in which alteration in gut microbiota induces carcinogenesis is a mechanism revealed for the first time by the present inventors. In light of the carcinogenic mechanism, a carcinogenic risk can be reduced by improving condition of gut microbiota. The reduction in carcinogenic risk is a major challenge to many countries including Japan having high cancer death rates.

The present invention is based on the finding that alteration in gut microbiota is related to cancer development, and an object of the present invention is to provide a method for screening for a food ingredient or a food composition that improves gut microbiota balance and reduces a carcinogenic risk.

Solution to Problem

The method of the present invention is a screening method which is carried out to select a food ingredient or a food composition that reduces a carcinogenic risk, comprising using gut microbiota and/or a product of a bacterium constituting the gut microbiota as an index.

The study of the present inventors has revealed that alteration in gut microbiota plays a role in the mechanism of cancer development. Thus, the food ingredient or the food composition can be screened for and selected by analyzing gut microbiota and/or a product of a bacterium constituting the gut microbiota as an index.

In a system using a laboratory animal, a candidate substance is administered as a candidate food ingredient or a candidate food composition for a given period, and alteration in gut microbiota may be analyzed by monitoring, or alteration in gut microbiota may be determined by using blood, feces, or the like and monitoring a substance produced by an intestinal bacterium.

In this context, the alteration in gut microbiota can be determined as the ratio between Gram-positive bacteria and Gram-negative bacteria in a sample collected from the laboratory animal.

Also, the alteration in gut microbiota can be determined as decrease in Gram-positive bacteria relative to Gram-negative bacteria in a sample collected from the laboratory animal.

Alternatively, the alteration in gut microbiota may be determined as increase or decrease in anaerobic bacteria in a sample collected from the laboratory animal.

The type of the bacterium to be monitored will be elucidated as the analysis of animal species used as a subject or the correlation between carcinogenesis and the type of a bacterium altered thereby will progress in the future.

In the screening method of the present invention, a candidate substance is added to a culture system of the intestinal bacterium, and the promotion of the proliferation or the inhibition of the proliferation of the bacterium can be used as an index. The proliferation inhibitory effect of the candidate substance on an intestinal bacterium that increases a carcinogenic risk or the proliferation-promoting effect of the candidate substance on an intestinal bacterium that reduces a carcinogenic risk can be analyzed.

In the screening method of the present invention, the bacterium is a bacterium belonging to the genus *Clostridium*.

Among intestinal bacteria, an anaerobic Gram-positive bacterium belonging to the genus *Clostridium*, particularly, a bacterium belonging to cluster XI of the genus *Clostridium*, is most preferably used as an index. The results of the analysis of the present inventors have revealed that among intestinal bacteria, an anaerobic intestinal bacterium, particularly, a bacterium belonging to cluster XI of the genus *Clostridium*, is increased. Therefore, the screening can be sensitively carried out with this as an index.

In the screening method of the present invention, a candidate substance is added to a culture system of the bacterium, and the inhibition of the proliferation of the bacterium is used as an index.

A larger number of candidate substances can be screened in a short time by using the intestinal bacterium culture system.

The candidate substances can be sensitively screened by using the intestinal bacterium culture system and, after addition of each candidate substance, using the proliferation of the bacterium or deoxycholic acid or lithocholic acid as an index.

In the screening method of the present invention, the product of the bacterium is at least one of deoxycholic acid and lithocholic acid, which are bile acid metabolites.

Under the carcinogenic mechanism elucidated by the present inventors, deoxycholic acid and lithocholic acid, which are secondary bile acids produced by intestinal bacteria, have been found to cause senescence and induce the malignant transformation of their adjacent cells.

Thus, a food ingredient or a food composition inhibiting the proliferation of an intestinal bacterium that increases a carcinogenic risk can be selected with these secondary bile acids as an index.

The screening method which is carried out to select a food ingredient or a food composition that reduces a carcinogenic risk according to the present invention, comprises continuously administering a candidate substance for a given period to an animal model having an altered gut microbiota, and using at least one of bile acid metabolites including deoxycholic acid and lithocholic acid as an index.

In this context, deoxycholic acid or lithocholic acid can be sensitively detected by using blood as a sample in the screening method using the laboratory animal.

The present invention also provides a food ingredient or a food composition obtained by any of the aforementioned screening methods.

The food ingredient or the food composition obtained by any screening method of the present invention improves gut microbiota balance and is therefore effective for reducing a carcinogenic risk.

BRIEF DESCRIPTION OF DRAWINGS

FIGS. 2A to 2C show the preparation of carcinogenesis models with multiple cancer caused by obesity using wild-type mice, and results thereof. FIG. 2A schematically shows the rearing schedule of the carcinogenesis models by high-fat diet feeding. FIG. 2B shows views about the livers of mice fed normal diets (ND) or high-fat diets (HFD). FIG. 2C shows the rate of cancer development in the mice fed normal diets or high-fat diets.

FIG. 4A schematically shows the rearing schedule of carcinogenesis models by high-fat diet feeding, wherein an antibiotic was administered to the carcinogenesis models. FIG. 4B shows alteration in the level of a gene encoding bacterial 16S rRNA by antibiotic administration. FIG. 4C shows the effect of antibiotic administration on liver cancer development and shows views about the livers of each group. FIG. 4D shows an average tumor number in the livers and size distribution thereof.

FIGS. 6A to 6D show the influence of deoxycholic acid on liver cancer development. FIG. 6A schematically shows the rearing schedule of mice fed high-fat diets and given an antibiotic cocktail, wherein deoxycholic acid was administered to the mice. FIG. 6B shows views about the livers of a control group (high-fat diet+antibiotic cocktail administration) and a deoxycholic acid administration group (high-fat diet+antibiotic cocktail administration+deoxycholic acid administration). FIG. 6C shows an average tumor number in the livers of each group and size distribution thereof. FIG. 6D shows the rates of expression of a senescence marker, a SASP-related marker, and a DNA damage marker in the hepatic stellate cells ($\alpha$-smooth muscle actin-positive cells) of the mice given deoxycholic acid.

FIGS. 8A to 8B show a liver cancer induction experiment in a sterile environment. FIG. 8A shows views about the livers of germ-free mice carrying no intestinal bacterium (Germ Free) and mice carrying indigenous bacteria (Control) at the age of 30 weeks, wherein the mice were treated with DMBA and then raised by high-fat diet feeding. FIG. 8B shows an average tumor number in the livers and size distribution thereof.

DESCRIPTION OF EMBODIMENTS

The study of the present inventors on the mechanism of cancer development using animal models has revealed that alteration in gut microbiota causes cancer development. The present invention is based on this finding and relates to a method for screening for a food ingredient that reduces a carcinogenic risk.

Figure 1:
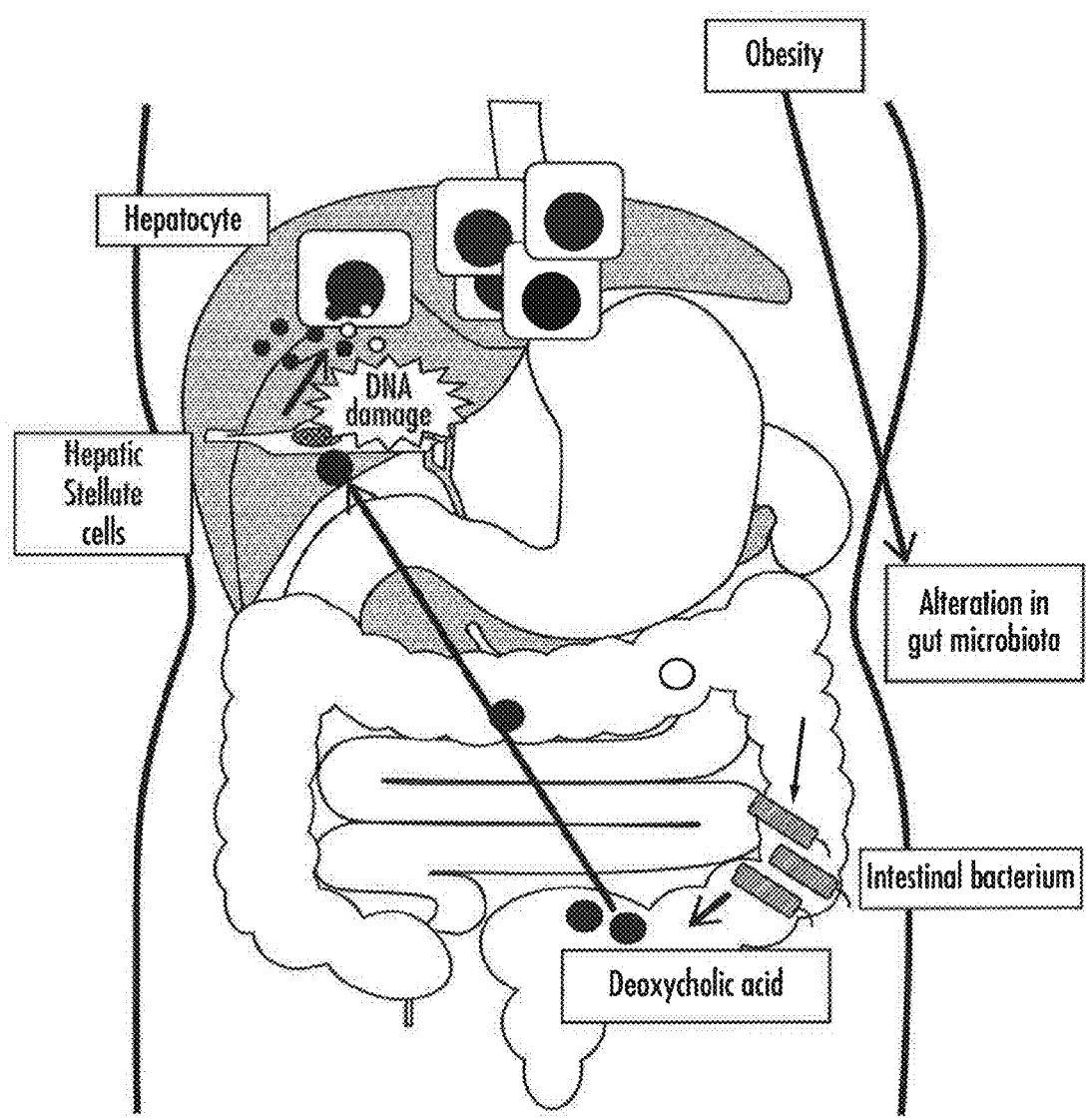
FIG. 1 schematically shows the mechanism of liver cancer development induced by obesity.

First, the carcinogenic mechanism related to alteration in gut microbiota elucidated by the present inventors will be described (FIG. 1). Gut microbiotas reflect the health conditions of their hosts. Therefore, a gut microbiota is altered due to alteration in the health condition of the individual, i.e., obesity in the case of FIG. 1.

In carcinogenesis models developed by the present inventors, the proportion of Gram-positive bacteria is significantly increased relative to Gram-negative bacteria. Among the Gram-positive bacteria, particularly, bacteria of cluster XI of the genus *Clostridium*, are increased.

The cluster XI of the genus *Clostridium* has an enzyme that converts a primary bile acid to a secondary bile acid deoxycholic acid by metabolism. The increased cluster XI of the genus *Clostridium* increases the concentration of deoxycholic acid in blood so that the deoxycholic acid is delivered to the liver through the portal vein.

The deoxycholic acid causes DNA damage via reactive oxygen species (ROS) production, and this DNA damage causes senescence.

In the mice with cancer, it was confirmed that senescence occurs in hepatic stellate cells, resulting in SASP. SASP factors secreted from hepatic stellate cells act on hepatocytes adjacent to the hepatic stellate cells to cause carcinogenesis.

As mentioned above, the present inventors have empirically demonstrated and elucidated each stage of the mechanism spanning multiple stages from alteration in gut microbiota to cancer development. On the basis of this mechanism, a food ingredient or a food composition capable of reducing a carcinogenic risk can be selected with the alteration in gut microbiota as an index.

[Cancer Targeted for Risk Reduction]

The present inventors have conducted analysis using mouse models whose carcinogenesis was induced by obesity and a carcinogenic substance. In light of the carcinogenic mechanism in which alteration in gut microbiota induces carcinogenesis, it should be understood that not only obesity but any state in which a gut microbiota is altered to throw the balance toward Gram-positive bacteria increases a carcinogenic risk.

SASP is a phenomenon found in association with senescence not only in hepatic stellate cells but in various types of cells and is known to be involved in the malignant transformation of cells in regions adjacent to the cells. The SASP phenomenon is recognized in various cells such as melanocytes, fibroblasts, and endothelial cells and in various tissues such as mammary glands, the prostate, and the skin (Non Patent Literature 9). It has been reported that SASP is also involved in the development of melanoma (Non Patent Literature 10). As shown in Examples, SASP is induced by deoxycholic acid through the bloodstream. Therefore, it can be understood that the induction of SASP also occurs in sites other than hepatic stellate cells of the liver in an individual having a high concentration in blood of a secondary bile acid such as deoxycholic acid.

The carcinogenesis models used in Examples are models whose carcinogenesis was induced by obesity and a carcinogenic substance. Any cancer can be targeted as long as the cancer is caused by SASP triggered by alteration in gut microbiota. Specifically, a carcinogenic risk can probably be reduced by ingesting a food comprising a food ingredient selected by the screening method according to the present invention. Cancers whose correlation with obesity has been epidemiologically pointed out in humans, including digestive organ cancers such as esophageal cancer, stomach cancer, gallbladder cancer, liver cancer, bile duct cancer, pancreatic cancer, and colorectal cancer, and lung cancer shown to be developed at an increased rate comparably with liver cancer in the carcinogenesis models of Example 1, are particularly preferably targeted.

The food ingredient selected by the screening method of the present invention, and a food comprising this food ingredient are effective for reducing a carcinogenic risk not only for those described above but for any cancer associated with alteration in gut microbiota.

[Subject or Animal for Food Ingestion]

The food comprising the food ingredient selected by the screening of the present invention is useful for any individual having a risk of cancer development.

For example, for a patient having a cancer which has already been treated, the recurrence of the cancer can be inhibited by keeping the gut microbiota in healthy conditions by the ingestion of the food comprising the food ingredient.

For a subject exhibiting indications pointing to alteration in gut microbiota, for example, an individual already diagnosed as having obesity from BMI values by medical checkup or the like, a carcinogenic risk can be reduced by keeping the gut microbiota in healthy conditions by the ingestion of the food comprising the food ingredient. Not only for an obese individual but for an individual indicating a high carcinogenic risk of a particular cancer, for example, an individual exhibiting indications such as fatty liver or NASH (non-alcoholic steatohepatitis) as to liver cancer or an individual smoking habitually as to lung cancer, carcinogenesis can be inhibited by keeping the gut microbiota in healthy conditions by the active ingestion of the food comprising the food ingredient.

In addition, even healthy individuals can keep their gut microbiotas in proper conditions by ingesting the food comprising the food ingredient on a routine basis. Therefore, their carcinogenic risks can be reduced.

In this context, the food comprising the food ingredient selected by the screening of the present invention is useful for any animal as long as a carcinogenic risk is increased by alteration in gut microbiota in the animal. Examples of the animal that is subject to ingestion include mammals such as humans, laboratory animals (e.g., mice, rabbits, rats, guinea pigs, and monkeys), pets (e.g., dogs and cats), and livestock (e.g., goats, cattle, and sheep).

[Screening Method]

On the basis of the mechanism spanning multiple stages from alteration in gut microbiota to cancer development elucidated by the present inventors, a compound having the effect of reducing a carcinogenic risk can be selected by a screening method illustrated below.

In this screening method, for example, a laboratory animal such as a mouse can be used with alteration in gut microbiota as an index, or an intestinal bacterium culture system or a cultured cell system of a carcinogenesis model can be used.

(Screening Method Using Laboratory Animal)

In a specific screening method, a laboratory animal having an altered gut microbiota is used, and a candidate substance is administered thereto for a given period. In this context, for example, the obese animal model system of Example 1 can be used as the laboratory animal having an altered gut microbiota. As described in Example 1, not only a mouse but any animal usually used, such as a rat or a rabbit, can be used as long as its gut microbiota can be altered by obesity.

In this context, the cancers in the carcinogenesis models were developed using a carcinogenic substance. For merely monitoring the alteration in gut microbiota, it is not necessarily required to induce carcinogenesis.

The gut microbiota may be artificially altered, for example, by feeding an animal with a diet mixed with a particular bacterium.

A candidate substance is administered to the laboratory animal as described above for a given period, and alteration in microbiota is detected in the laboratory animal.

Particularly, for the purpose of selecting a food ingredient, a food itself expected to improve condition of gut microbiota may be used as the candidate substance, or a particular food ingredient or candidate compound may be used as the candidate substance. In the case of using a laboratory animal, the animal may be fed with a diet or drinking water mixed therewith, or a given amount thereof may be forcedly administered to the animal using a syringe or the like.

The alteration in gut microbiota can be detected from, for example, alteration in the ratio between Gram-positive bacteria and Gram-negative bacteria. The ratio between Gram-positive bacteria and Gram-negative bacteria may be detected by detecting any one of Gram-positive bacteria or Gram-negative bacteria. Examples of the Gram-positive bacterium to be detected can include bacterium belonging to the genus *Clostridium*, the genus *Peptostreptococcus*, the genus *Eubacterium*, the genus *Staphylococcus*, the genus *Enterococcus*, the genus *Micrococcus*, the genus *Bacillus*, and the genus *Mycobacterium*. A bacterium belonging to the genus *Clostridium* is preferred.

In the case of using the bacterium belonging to the genus *Clostridium* as an index, all bacteria belonging to the genus *Clostridium* may be detected. Alternatively, one or more bacteria belonging to the genus *Clostridium* or bacteria belonging to a particular cluster of the genus *Clostridium* may be detected. Particularly, bacteria belonging to cluster XI of the genus *Clostridium* produce deoxycholic acid inducing senescence or exhibit a significantly increased ratio in carcinogenesis mouse models. For these reasons, the food ingredient having the effect of reducing a carcinogenic risk can probably be detected with high accuracy.

Also, the food ingredient having the effect of reducing a carcinogenic risk can be detected with high accuracy by detecting other bacteria producing deoxycholic acid, for example, a bacterium belonging to the genus *Bacteroides*.

The alteration in gut microbiota can also be analyzed by assaying a substance produced by the intestinal bacterium.

In the case of analyzing the ratio between Gram-positive bacteria and Gram-negative bacteria, a substance produced by a Gram-positive bacterium and a substance produced by a Gram-negative bacterium may both be assayed, or any of them may be assayed alone. For example, bacteria belonging to the genus *Clostridium*, including bacteria belonging to cluster XI of the genus *Clostridium*, have 7α-dehydrogenase, which mediates the production of secondary bile acids from primary bile acids. Therefore, the secondary bile acids can be to be measured. Examples of the secondary bile acids include deoxycholic acid and lithocholic acid. Deoxycholic acid is preferred.

In the screening method using a laboratory animal, the sample in which the gut microbiota is analyzed is not particularly limited as long as the sample is collected from the laboratory animal and contains an intestinal bacterium. The sample is preferably, for example, feces, urine, sputum, a gastrointestinal fluid, a gastrointestinal lavage, a lung lavage, a tracheal lavage, saliva, an oral lavage, or a biopsy sample and is more preferably feces or saliva, most preferably feces, in consideration of burdens on the laboratory animal and handling.

In the case of measuring the substance produced by the intestinal bacterium, the sample is not particularly limited as long as the sample is collected from the laboratory animal and contains the substance produced by the intestinal bacterium. The sample is preferably, for example, blood, feces, urine, sputum, a gastrointestinal fluid, a gastrointestinal lavage, a lung lavage, a tracheal lavage, saliva, an oral lavage, or a biopsy sample and is more preferably feces, urine, saliva, or blood, most preferably blood, in consideration of burdens on the laboratory animal, handling, and detection sensitivity.

In this context, since the secondary bile acid produced by the intestinal bacterium is related to carcinogenesis as shown in Examples, not only the laboratory animal having a altered gut microbiota but a laboratory animal having an increased secondary bile acid concentration in blood may be used to select a compound having the effect of decreasing the secondary bile acid concentration in blood.

(Screening Method Using Culture System)

A larger number of candidate substances can be screened in a short time by use of an intestinal bacterium culture system than use of the laboratory animal.

Specifically, for example, an intestinal bacterium highly correlating with a carcinogenic risk is cultured by a method well known to those skilled in the art, and each candidate substance is allowed to act thereon. Whether or not the candidate substance has the effect of reducing a carcinogenic risk can be determined with the proliferation of this intestinal bacterium as an index. When the intestinal bacterium is, for example, a bacterium increasing the carcinogenic risk, a substance inhibiting its proliferation can be selected. On the other hand, when the intestinal bacterium is a bacterium reducing the carcinogenic risk, a substance promoting its proliferation can be selected.

Alternatively, whether or not the candidate substance has the effect of reducing a carcinogenic risk can be determined with a secondary bile acid produced by the intestinal bacterium as an index. Alternatively, whether or not the candidate substance has the effect of reducing a carcinogenic risk can be determined with the secondary bile acid-producing activity of the intestinal bacterium as an index.

In addition, the candidate substances can also be screened by use of a cultured cell system of a carcinogenesis model.

Specifically, each candidate substance is added to, for example, culture medium of cultured cells, and a secondary bile acid is allowed to act thereon to induce senescence. On the basis of whether or not the cultured cells actually exhibit senescence by the action of the secondary bile acid, the candidate substance can be judged as having or not having the effect of inhibiting or suppressing the activity of the secondary bile acid, i.e., can be judged as having or not having the effect of reducing a carcinogenic risk. In consideration of the accuracy of screening, the cultured cells are preferably cultured cells derived from the animal species and cancer type of an actual subject for which the carcinogenic risk is to be reduced. In this context, the presence or absence of senescence can be examined by assaying a SASP factor in the culture medium or using a well-known index for senescence, such as the presence or absence of the expression of a senescence marker.

(Method for Evaluating Candidate Substance)

In the screening method using the laboratory animal and the screening method using the cultured cell system as mentioned above, the alteration in gut microbiota can be appropriately analyzed using a reagent capable of distinguishing between Gram-positive bacteria and Gram-negative bacteria, for example, a Gram staining agent or PCR primers distinguishing between Gram-positive bacteria and Gram-negative bacteria. In the case of using PCR, primers for detection, PCR conditions, etc., can be designed and set by those skilled in the art. In the case of detecting, for example, the bacteria belonging to cluster XI of the genus *Clostridium*, primers specific for the cluster XI of the genus *Clostridium* described in Non Patent Literature 9 can also be used.

In this context, the assay of the substance produced by the intestinal bacterium is not limited as long as the substance can be detected. Examples thereof include methods by chromatography such as gas chromatography, mass spectrometry, and detection methods using specific antibodies. Detection conditions, etc., for these detection methods can be appropriately set by those skilled in the art.

The candidate substance that produces desired effects can be selected by analysis using the aforementioned evaluation method.

[Food and Prevention Method]

The food ingredient or the food composition selected by the screening method of the present invention reduces a carcinogenic risk and as such, can be used as a food for carcinogenesis prevention.

Such a food is particularly effective for being given to an individual considered to have a high carcinogenic risk, for example, an individual exhibiting indications pointing to alteration in gut microbiota, such as an individual already diagnosed as having obesity from BMI values by medical checkup or the like. Alternatively, the food is effective for being given to an individual indicating a high carcinogenic risk of a particular cancer, for example, individual exhibiting indications such as fatty liver or NASH (non-alcoholic steatohepatitis) as to liver cancer or an individual smoking habitually as to lung cancer Of intestinal bacteria confirmed to be related to a carcinogenic risk, an intestinal bacterium itself that reduces a carcinogenic risk can also be used as a food ingredient in a food for reducing a carcinogenic risk or for preventing carcinogenesis.

The food ingredient according to the present invention may be used, for example, together with an additional food ingredient, and processed into any food form such as yogurt, a solution (e.g., soft drink or soup), a capsule, a chewable tablet, or powders.

The recipient animal is not particularly limited as long as the animal is related to alteration in gut microbiota and carcinogenesis. Preferred examples thereof include mammals such as humans, laboratory animals (e.g., mice, rabbits, rats, guinea pigs, and monkeys), pets (e.g., dogs and cats), and livestock (e.g., goats, cattle, and sheep). A human is particularly preferred.

Example 1: Preparation of Carcinogenesis Model with Multiple Cancer

FIG. 2A shows a method for preparing carcinogenesis models used in the present invention. An acetone solution containing 0.5% of the carcinogenic substance DMBA (7,12-dimethylbenz[a]anthracene) was applied once to the backs of wild-type (C57BL/6) neonatal mice. The neonatal mice were raised together with their mother mouse by feeding with normal diets (ND) or high-fat diet (HFD) until 4 weeks old. The high-fat diets used were D12492 (Rodent Diet with 60% kcal % Fat; Research Diets, Inc., USA). The neonatal mice were weaned at 4 weeks old and subsequently raised with normal diets or high-fat diet. At 30 weeks old, their livers and lungs were excised, and the presence or absence of cancer development was analyzed. The average body weight of the mice at the time of dissection was 33 g for the mice fed normal diets and 51 g for the mice fed high-fat diets. The mice fed high-fat diets had approximately 1.5 times the body weights of the mice fed normal diets.

FIG. 2B shows the typical views from dissection about the livers of the mice fed normal diets or high-fat diet. The livers of the mice fed high-fat diets were enlarged into fatty livers and had multiple liver cancer (indicated by Δ).

FIG. 2C shows the rate of cancer development due to the diets. In the mice fed normal diets (n=9), 5% mice developed lung cancer, whereas 95% mice showed no cancer development. By contrast, in the mice fed high-fat diets (n=18), 68% mice developed liver cancer, and 32% mice concurrently developed both liver cancer and lung cancer.

The carcinogenesis mouse models of the present invention develop liver cancer at a rate as high as 100% rate. Thus, the carcinogenesis mouse models of the present invention can be used to analyze and screen with high accuracy the effects of food ingredients or food compositions given as diets.

This indicates that the mice rendered obese by high-fat diet feeding have multiple liver cancer and lung cancer. The present inventors have also obtained similar results by use of ob/ob mice known as genetically obese mice. Specifically, the ob/ob neonatal mice similarly have multiple liver cancer when treated with DMBA and then raised with normal diets.

Since cancer development can be induced in 30 weeks using these carcinogenesis mouse models, candidate substances inhibiting carcinogenesis can be efficiently screened in a relatively short time as a system using laboratory animals to select the compound of interest. Specifically, a food ingredient inhibiting a cancer can be screened by administering each candidate substance either at any point in time or continuously in the rearing schedule shown in FIG. 2A and analyzing its effect on cancer development.

Example 2: SASP Induction by Senescence of Hepatic Stellate Cell and Liver Cancer Development Recently, it has been suggested that some secreted factors increase a risk of cancer development, and substances classified into SASP factors are included therein (Non Patent Literature 8).

Results of previous analysis revealed that cells secreting SASP factors in the liver are hepatic stellate cells. Thus, the livers of the mice fed high-fat diets and the mice fed normal diets were subjected to cell staining to analyze whether senescence occurred in their hepatic stellate cells and SASP was observed.

Double staining was carried out using the cell marker α-smooth muscle actin for hepatic stellate cells and p21 or p16 as the marker of inducing senescence, the foci of 53BP1 or γH2AX as the marker of involved in DNA damage response, IL-6, Gro-α, or CXCL9 as the principal SASP factor to analyze senescence and the ratio of hepatic stellate cells secreting SASP factors.

Figure 3:
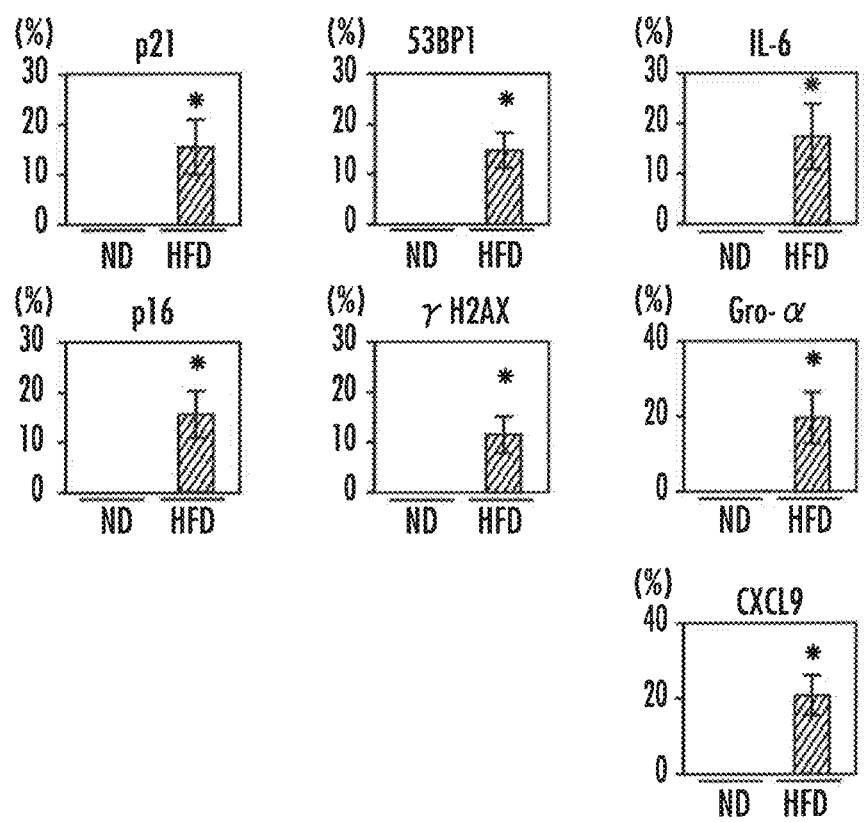
FIG. 3 shows the rates of expression of a senescence marker, a SASP-related marker, and a DNA damage marker in the hepatic stellate cells ($\alpha$-smooth muscle actin-positive cells) of the mice fed normal diets or high-fat diets.

The results are shown in FIG. 3. The expression of p21 and p16 inducing senescence and the foci of 53BP1 and γH2AX involved in DNA damage response were observed in the livers of the mice fed high-fat diets, whereas the expression of these proteins was not observed in the hepatic stellate cells of the mice fed normal diets. In addition, it was shown that the senescence occur in the hepatic stellate cells of the mice fed high-fat diets and the SASP factors are secreted from the hepatic stellate cells by the expression of IL-6, Gro-α, and CXCL9.

Also, p21-p-luc mice that permitted noninvasive observation of the expression of the senescence-inducing factor p21$^{Waf1/Cip1}$ were used in the liver cancer induction experiment by high-fat diet feeding after DMBA treatment in the same way as in the carcinogenesis models of Example 1. The expression of p21$^{Waf1/Cip1}$ was observed by bioluminescence imaging.

Although the data is not shown herein, the expression of p21$^{Waf1/Cip1}$ was observed in the regions of liver cancer, showing the correlation between senescence and liver cancer development.

These results indicate that: SASP occurs by the senescence of hepatic stellate cells; and SASP is closely related to liver cancer development.

Example 3: Carcinogenesis Inhibitory Effect by Improvement in Condition of Gut Microbiota FIG. 4A shows the experimental schedule. DMBA was applied to wild-type neonatal mice, followed by high-fat diet feeding. From 13 weeks old, an antibiotic cocktail (4Abx, antibiotic cocktail administration group) or vancomycin (VCM, vancomycin administration group) mixed with drinking water was administered to the mice. At the 30th week after the start of the raising, their livers were excised, and liver cancer development was analyzed. On the other hand, the raising of a control group was continued in the same way as the aforementioned raising up to the 13th week. The antibiotic cocktail contained ampicillin (1 g/l), neomycin (1 g/l), metronidazole (1 g/l), and vancomycin (500 mg/l). Also, in the case of administering vancomycin alone, 500 mg/l was administered.

Figure 4B:
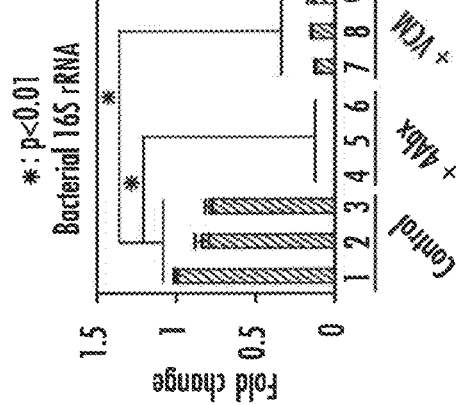
FIGS. 4A to 4D show alteration in the rate of liver cancer development by antibiotic administration.

FIG. 4B shows the level of a gene encoding intestinal bacterial 16s rRNA of 17 weeks after antibiotic administration, i.e., 30 weeks after birth. It was shown that the amount of intestinal bacteria was completely decreased by the antibiotic cocktail and also decreased into a very small level by vancomycin.

Figure 4D:
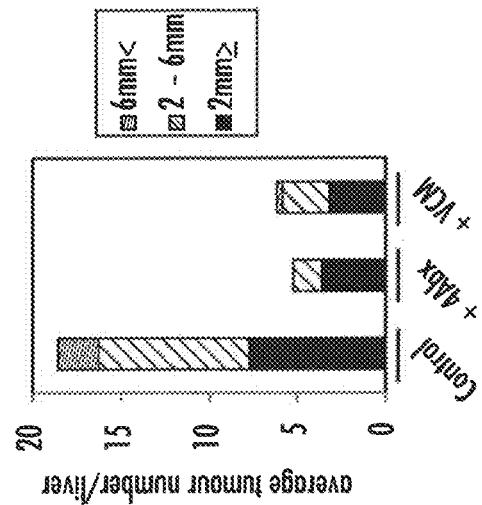
Figure 4A:
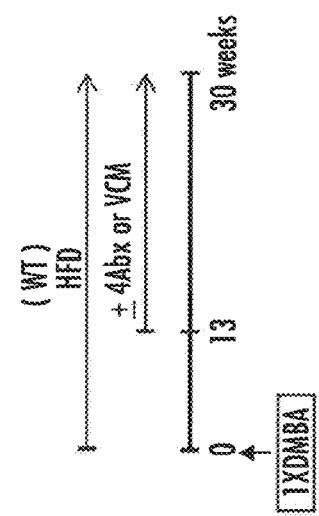
Figure 4C:
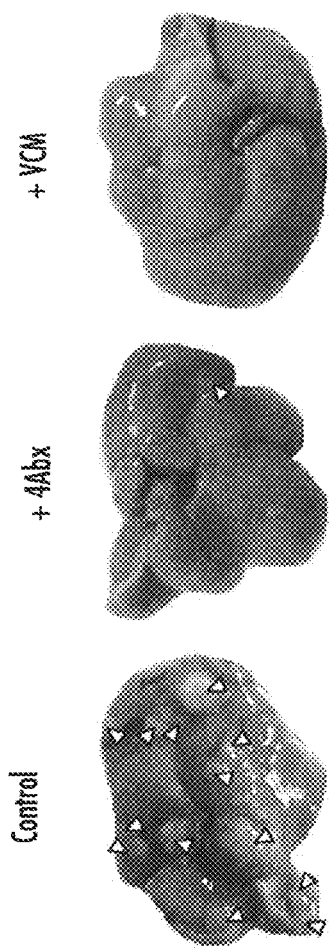

The mice of each group were dissected at the 30th week, and liver cancer development was analyzed (FIGS. 4C and 4D). Liver cancer development was observed in the control group, whereas the antibiotic cocktail administration group or the vancomycin administration group developed no liver cancer or developed liver cancer with a smaller tumor number and a smaller size as compared with the control.

These results indicate that the state of a gut microbiota before cancer development induces a cancer. Thus, if the state of a gut microbiota prior to cancer development can be improved by an ingested food, the cancer development can be inhibited.

In the present Examples, the antibiotic mixed with drinking water was continuously administered to the mice after weaning. A candidate substance may be mixed with diets and given to the mice. Depending on the water solubility or dose of the candidate substance, the candidate substance may be mixed with drinking water or may be mixed with diets. Alternatively, a given amount thereof may be forcedly orally administered using a syringe or the like.

As for the administration period, the administration can also be appropriately carried out according to the candidate substance. In the case of a substance that is secreted into mother milk, the mice may be exposed from birth to the candidate substance by mixing diets or drinking water therewith for mother mice.

As described above, a food ingredient that reduces carcinogenic risk can be screened for by using the experimental system of the present invention and forcedly administering each candidate substance or feeding the mice with diets or drinking water mixed therewith.

Although C57BL/6 was used as the carcinogenesis mouse models, a mouse of any lineage can be used as a matter of course. In the present Examples, the analysis was conducted using the mice. Other laboratory animals generally used, such as rats or rabbits, may be given high-fat diets and used to analyze alteration in gut microbiota.

Example 4: Search for Intestinal Bacterium Related to Cancer Development

Next, alteration in gut microbiota caused by antibiotic administration conducted in Example 3 will be shown. In the experimental schedule shown in FIG. 4A, 3 groups were used: a group fed normal diets, a group fed high-fat diets, and a group fed high-fat diets and also given vancomycin. The gut microbiota was analyzed.

The gut microbiota was identified by PCR analysis (Non Patent Literatures 11 and 12). Specifically, DNA was extracted from the feces and purified. The gene encoding 16S rRNA in many types of bacteria was amplified by PCR using universal primers. The V1-V4 hypervariable regions were further amplified, followed by identification.

In the group fed normal diets (n=5), 54% to 79% Gram-negative bacteria and 20.9 to 45% Gram-positive bacteria (of which, cluster XI of the genus *Clostridium*: 0%) were found. In the group fed high-fat diets (n=4), 1.5 to 22% Gram-negative bacteria and 77.4 to 98.4% Gram-positive bacteria (of which, cluster XI of the genus *Clostridium*: 3.4 to 18%) were found. In the group given vancomycin (n=2), 98 to 99.8% Gram-negative bacteria and 0 to 1.9% Gram-positive bacteria (of which, cluster XI of the genus *Clostridium*: 0%) were found.

Figure 5:
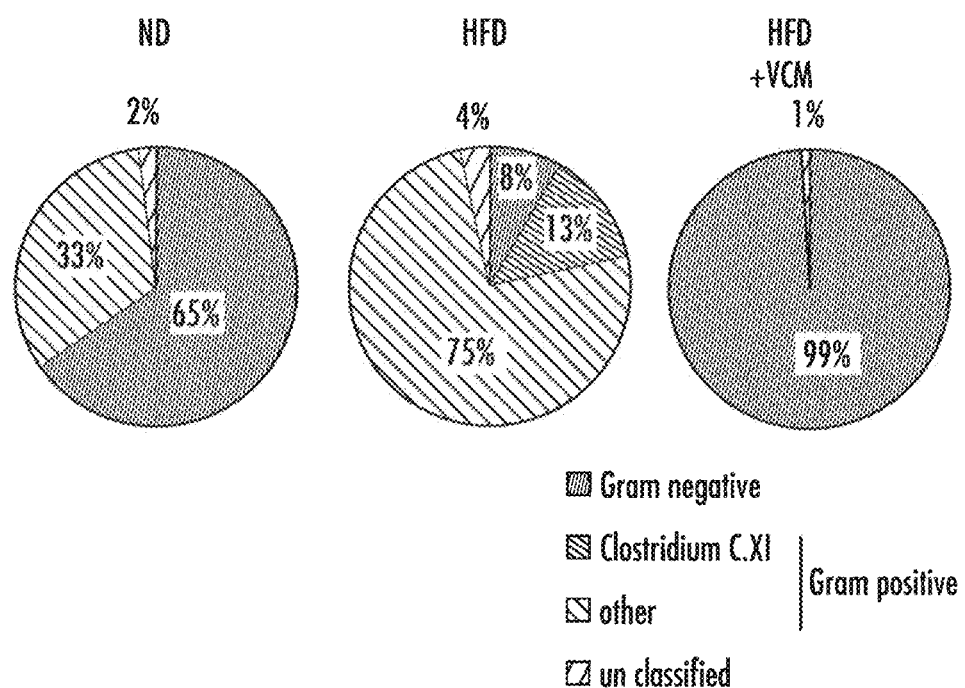
FIG. 5 shows alteration in gut microbiota by obesity.

The average values of these ratios are shown in FIG. 5. The mouse group fed normal diets (ND) contained 65% Gram-negative bacteria on average, whereas the Gram-negative bacteria were significantly decreased to 8% on average in the mouse group fed high-fat diets (HFD) which instead contained 88% Gram-positive bacteria on average. Among the Gram-positive bacteria, cluster XI of the genus *Clostridium* accounted for a very large proportion (13% on average).

In the mouse group fed high-fat diets and also given vancomycin (HFD+VCM), Gram-negative microbiota accounted for the substantial proportion (99% on average).

Such alteration in gut microbiota was compared with cancer development, showing that the increased ratio of Gram-positive bacteria correlates with an increased risk of liver cancer development. In addition, it was shown that the increased ratio of bacteria of cluster XI of the genus *Clostridium* correlates with an increased risk of liver cancer development.

From the correlation between alteration in gut microbiota and cancer development, a risk of cancer development is found to be increased by increase in the ratio of Gram-positive bacteria.

As seen from these results, candidate substances can be screened by analyzing the ratio between Gram-negative bacteria and Gram-positive bacteria in a gut microbiota. Increase in Gram-positive bacteria in the gut microbiota indicates a rise in carcinogenic risk in the intestinal environment. Thus, candidate substances can be screened with the ratio between Gram-negative bacteria and Gram-positive bacteria or increase in Gram-positive bacteria as an index.

Figure 7A:
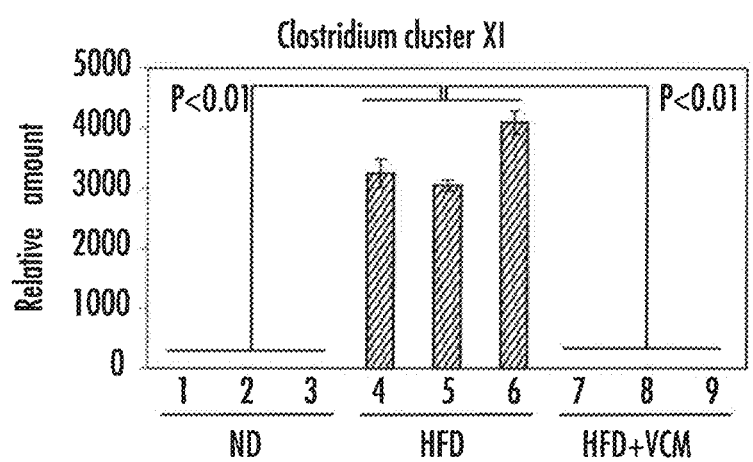
FIG. 7A shows the effect of antibiotic administration on intestinal bacteria and cluster XI of the genus *Clostridium*.
Figure 7B:
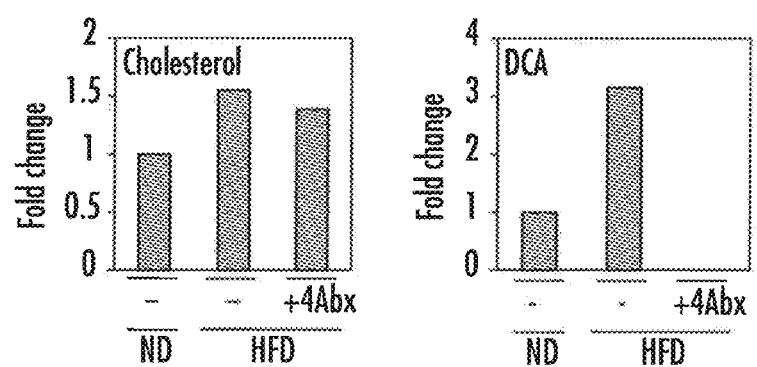
FIG. 7B shows the effect of antibiotic administration on cholesterol (left) and deoxycholic acid (right).

As shown in FIG. 4, the antibiotic administration inhibited cancer development and also decreased the amount of cluster XI of the genus *Clostridium* (FIGS. 5 and 7A). Also, the antibiotic administration decreased the amount of deoxycholic acid in blood (FIG. 7B).

Example 5: Induction of Carcinogenesis Mediated thorough SASP by Deoxycholic Acid From the 13th week after the start of the raising, the antibiotic cocktail was administered to mice fed high-fat diets, which were then further raised. To these mice, 40 μg/g body weight of deoxycholic acid (DCA) or only a vehicle as a control was orally administered three times a week (FIG. 6A).

FIG. 6B shows typical views about the livers of both groups. The mice given deoxycholic acid developed a large number of liver tumors (indicated by Δ in the diagram), whereas cancer development was rarely seen in the control mouse group given only the vehicle. FIG. 6C shows an average tumor number per liver of an individual, and the size thereof (n=3). The cancer was rarely developed in the control mouse group given only the vehicle, and even if the cancer was developed, its tumor size was small. On the other hand, the deoxycholic acid administration group had multiple cancer (25 or more tumors per individual), and also, its size was large.

The aforementioned analysis showed that deoxycholic acid causes liver cancer development.

The deoxycholic acid in the blood of these mice was assayed. As a result, the mice fed high-fat diets had 3 times more concentrations of the deoxycholic acid than that of the mice fed normal diets, whereas deoxycholic acid was detected at a level below the limit in the mice fed high-fat diets and also given the antibiotic cocktail (FIG. 7B).

Thus, it can be predicted that a carcinogenic risk is increased even if the deoxycholic acid concentration in blood is a few times that of healthy subjects.

Although the data is not shown herein, cultured hepatic stellate cells were cultured in a 10% Dulbecco's modified Eagle's medium (supplemented with 10% FBS, 3% $O_2$, 5% $CO_2$), and 200 μM of deoxycholic acid was added thereto. As a result, increase in reactive oxygen species (ROS) causing senescence or the expression of SASP-related factors was confirmed. This implies that a carcinogenic risk is increased even if having a very low concentration.

It was further confirmed using an immunostaining method that deoxycholic acid delivered to the liver induces SASP in hepatic stellate cells.

As shown in FIG. 6D, p21 known to induce SASP and the SASP factors IL-1β, IL-6, and Gro-α were expressed in the deoxycholic acid administration group, whereas no expression thereof was confirmed in the control group.

Example 6: Carcinogenic Risk Based on Presence or Absence of Gut Microbiota

As shown in Examples 3 and 4, a risk of liver carcinogenesis was found to be reduced by decreasing the number of intestinal bacteria by antibiotic administration. Thus, mice were raised in a sterile environment carrying no intestinal bacterium, and neonatal mice were treated with DMBA and raised with high-fat diets in the same way as in Example 1. At the age of 30 weeks, the presence or absence of liver cancer development was analyzed in obese mice whose body weight reached 45 g or more.

Since germ-free mice were less likely to be obese because of the absence of intestinal bacteria, as compared with mice having indigenous bacteria (average body weight: approximately 57 g), and had an average body weight of approximately 48 g.

FIG. 8A shows typical views about the livers of mice in each group. In FIG. 8A, liver cancer is indicated by Δ. FIG. 8B shows an average tumor number per liver of an individual, and the size thereof. An average value from 6 individuals for the control mice and 9 individuals for the germ-free mice are shown.

Liver cancer development was seen in the mice having indigenous bacteria (control mice), whereas cancer development was inhibited in the germ-free mice, albeit obese, carrying no gut microbiota.

The results about the germ-free mice, albeit obese, having a low risk of liver cancer development indicate that the presence or absence of intestinal bacteria correlates with liver cancer development. In consideration of the results of Example 5, the intestinal bacteria are found to produce secondary bile acids and be deeply involved in liver cancer development.

As shown above, carcinogenesis can be inhibited by administering a substance that alters a gut microbiota. In the present Examples, the antibiotic shown to alter a gut microbiota was used. A novel substance that reduces a carcinogenic risk can be screened for by selecting a candidate substance that exhibits similar effects on intestinal bacteria.

In the present Examples, the system using carcinogenesis mouse models was mainly shown. A system may be established using ordinary mice because alteration in gut microbiota is used as an index. Also, a screening system can be established using a bacterium, cell line, or the like, producing secondary bile acids, as a matter of course. Not only the alteration in gut microbiota but any alteration in secondary bile acid, SASP-related factor, or the like in association with carcinogenesis suggested from the carcinogenic mechanism elucidated by the present inventors can be used as an index.

The food ingredient or the food composition obtained by the screening method of the present invention can be empirically shown to reduce a carcinogenic risk by using the animal models developed by the present inventors. Thus, an effective food ingredient or food composition can be screened for in a short time.

The invention claimed is:

1. A screening method for selecting a food ingredient or a food composition that reduces a carcinogenic risk, the method comprising:

administering a candidate food ingredient or a candidate food composition to a laboratory animal;

collecting a sample from the laboratory animal after administration of the candidate food ingredient or the candidate food composition;

determining from the sample collected from the laboratory animal whether an alteration in gut microbiota has occurred as a result of the administration of the candidate food ingredient or the candidate food composition to the laboratory animal; and selecting the candidate food ingredient or the candidate food composition where the alteration in the gut microbiota is determined to be a decrease in Gram-positive bacteria relative to Gram-negative bacteria.

2. The screening method according to claim 1, wherein the Gram-positive bacteria belongs to the genus *Clostridium*.

3. A screening method for selecting a food ingredient or a food composition that reduces a carcinogenic risk, the method comprising:
   continuously administering a candidate food ingredient or a candidate food composition for a given period to an animal model having an altered gut microbiota;
   collecting samples from the animal model after administration of the candidate food ingredient or the candidate food composition;
   determining from the samples collected from the animal model whether there has been a change to the altered gut microbiota as a result of the continuous administration of the candidate food ingredient or the candidate food composition to the animal model; and
   selecting the candidate food ingredient or the candidate food composition where the change to the altered gut microbiota is determined to be a decrease in Gram-positive bacteria relative to Gram-negative bacteria.

4. The screening method according to claim 3, wherein the animal model having the altered gut microbiota is a mouse that has been fed a high-fat diet.

* * * * *